US008465938B2

(12) United States Patent
Ohmiya et al.

(10) Patent No.: US 8,465,938 B2
(45) Date of Patent: Jun. 18, 2013

(54) **METHOD FOR PRODUCING COMPLEX OF BIOTIN-LABELED *CYPRIDINA* (*CYPRIDINA NOCTILUCA*) LUCIFERASE WITH STREPTOAVIDIN AND METHOD FOR STABILIZING THE SAME**

(75) Inventors: Yoshihiro Ohmiya, Ikeda (JP); Chun Wu, Ikeda (JP); Satoru Ohgiya, Sapporo (JP); Kosei Kawasaki, Sapporo (JP)

(73) Assignee: National Institute of Advanced Industrial Science and Technolgy, Tokyo-To (JP)

(*) Notice: Subject to any disclaimer, the term of this patent is extended or adjusted under 35 U.S.C. 154(b) by 237 days.

(21) Appl. No.: 12/959,729

(22) Filed: Dec. 3, 2010

(65) Prior Publication Data

US 2012/0077205 A1    Mar. 29, 2012

Related U.S. Application Data

(62) Division of application No. 11/692,134, filed on Mar. 27, 2007, now abandoned.

(60) Provisional application No. 60/833,182, filed on Jul. 24, 2006, provisional application No. 60/851,422, filed on Oct. 13, 2006.

(51) Int. Cl.
*G01N 33/53* (2006.01)

(52) U.S. Cl.
USPC .............................. 435/7.5; 435/7.1; 435/7.92

(58) Field of Classification Search
None
See application file for complete search history.

(56) References Cited

U.S. PATENT DOCUMENTS

| 2006/0024757 | A1* | 2/2006 | Hussa et al. ................... 435/7.2 |
| 2007/0254311 | A1 | 11/2007 | Alagic et al. |
| 2008/0076118 | A1 | 3/2008 | Tooke et al. |
| 2010/0221703 | A1* | 9/2010 | West et al. ........................ 435/6 |

FOREIGN PATENT DOCUMENTS

| EP | 0 141 581 | 5/1985 |
| JP | 60-138463 | 7/1985 |
| JP | 4-99500 | 3/1992 |
| JP | 05-064583 | 3/1993 |
| JP | 05-113443 | 5/1993 |
| JP | 07-098316 | 4/1995 |
| JP | 08-262021 | 10/1996 |

OTHER PUBLICATIONS

Zalipsky, Samuel. Chemistry of polyethylene glycol conjugates with biolgically active molecules. Advanced Drug Delivery Reviews 1994, vol. 16, pp. 157-182.*
Immunoassays, Pierce catalog. 1994, pp. 1-4.*
Kobayashi, Kouji, "The enzymatic vharacteristics and active formation of the luminous enzyme from the marine ostracod", Reports of the Graduate School of Electronic Science and Technology, vol. 25, 2004, pp. 141-143.
Diamandis, Eleftherios P., et al., "The Biotin-(Strept)Avidin System: Principles and Applications in Biotechnology", Clinical Chemistry, vol. 37, No. 5, 1991, pp. 625-636.

* cited by examiner

*Primary Examiner* — Shafiqul Haq
(74) *Attorney, Agent, or Firm* — Wenderoth, Lind & Ponack, L.L.P.

(57) ABSTRACT

The present invention relates to a method for producing *Cypridina* luciferase labeled with hydrophilic biotin, characterized in that a biotin reagent containing a polyalkylene glycol structure as a spacer is reacted with *Cypridina* luciferase, and biotin-labeled *Cypridina* luciferase wherein a sugar chain in *Cypridina* luciferase has been biotinylated.

3 Claims, 4 Drawing Sheets

SEQUENCE LISTING

```
<160> NUMBER OF SEQ ID NOS: 5

<210> SEQ ID NO 1
<211> LENGTH: 636
<212> TYPE: PRT
<213> ORGANISM: Cypridina Luciferase

<400> SEQUENCE: 1

Met Arg Phe Pro Ser Ile Phe Thr Ala Val Leu Phe Ala Ala Ser Ser
1               5                   10                  15

Ala Leu Ala Ala Leu Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45
```

```
Asp Val Ala Val Leu Pro Phe Ser Asn Ser Thr Asn Gly Leu Leu
 50                  55                  60

Phe Ile Asn Thr Thr Ile Ala Ser Ile Ala Ala Lys Glu Glu Gly Val
 65                  70                  75                  80

Ser Leu Glu Lys Arg Glu Ala Glu Ala Gln Asp Cys Pro Tyr Glu Pro
                 85                  90                  95

Asp Pro Pro Asn Thr Val Pro Thr Ser Cys Glu Ala Lys Glu Gly Glu
                100                 105                 110

Cys Ile Asp Ser Ser Cys Gly Thr Cys Thr Arg Asp Ile Leu Ser Asp
            115                 120                 125

Gly Leu Cys Glu Asn Lys Pro Gly Lys Thr Cys Cys Arg Met Cys Gln
        130                 135                 140

Tyr Val Ile Glu Cys Arg Val Glu Ala Ala Gly Trp Phe Arg Thr Phe
145                 150                 155                 160

Tyr Gly Lys Arg Phe Gln Phe Gln Glu Pro Gly Thr Tyr Val Leu Gly
                165                 170                 175

Gln Gly Thr Lys Gly Gly Asp Trp Lys Val Ser Ile Thr Leu Glu Asn
            180                 185                 190

Leu Asp Gly Thr Lys Gly Ala Val Leu Thr Lys Thr Arg Leu Glu Val
        195                 200                 205

Ala Gly Asp Ile Ile Asp Ile Ala Gln Ala Thr Glu Asn Pro Ile Thr
210                 215                 220

Val Asn Gly Gly Ala Asp Pro Ile Ile Ala Asn Pro Tyr Thr Ile Gly
225                 230                 235                 240

Glu Val Thr Ile Ala Val Val Glu Met Pro Gly Phe Asn Ile Thr Val
                245                 250                 255

Ile Glu Phe Phe Lys Leu Ile Val Asp Ile Leu Gly Gly Arg Ser
            260                 265                 270

Val Arg Ile Ala Pro Asp Thr Ala Asn Lys Gly Met Ile Ser Gly Leu
        275                 280                 285

Cys Gly Asp Leu Lys Met Met Glu Asp Thr Asp Phe Thr Ser Asp Pro
290                 295                 300

Glu Gln Leu Ala Ile Gln Pro Lys Ile Asn Gln Glu Phe Asp Gly Cys
305                 310                 315                 320

Pro Leu Tyr Gly Asn Pro Asp Asp Val Ala Tyr Cys Lys Gly Leu Leu
                325                 330                 335

Glu Pro Tyr Lys Asp Ser Cys Arg Asn Pro Ile Asn Phe Tyr Tyr Tyr
            340                 345                 350

Thr Ile Ser Cys Ala Phe Ala Arg Cys Met Gly Gly Asp Glu Arg Ala
        355                 360                 365

Ser His Val Leu Leu Asp Tyr Arg Glu Thr Cys Ala Ala Pro Glu Thr
370                 375                 380

Arg Gly Thr Cys Val Leu Ser Gly His Thr Phe Tyr Asp Thr Phe Asp
385                 390                 395                 400

Lys Ala Arg Tyr Gln Phe Gln Gly Pro Cys Lys Glu Ile Leu Met Ala
                405                 410                 415

Ala Asp Cys Phe Trp Asn Thr Trp Asp Val Lys Val Ser His Arg Asn
            420                 425                 430

Val Asp Ser Tyr Thr Glu Val Glu Lys Val Arg Ile Arg Lys Gln Ser
        435                 440                 445

Thr Val Val Glu Leu Ile Val Asp Gly Lys Gln Ile Leu Val Gly Gly
450                 455                 460

Glu Ala Val Ser Val Pro Tyr Ser Ser Gln Asn Thr Ser Ile Tyr Trp
```

```
                465                 470                 475                 480
Gln Asp Gly Asp Ile Leu Thr Thr Ala Ile Leu Pro Glu Ala Leu Val
                    485                 490                 495
Val Lys Phe Asn Phe Lys Gln Leu Leu Val Val His Ile Arg Asp Pro
                500                 505                 510
Phe Asp Gly Lys Thr Cys Gly Ile Cys Gly Asn Tyr Asn Gln Asp Phe
            515                 520                 525
Ser Asp Asp Ser Phe Asp Ala Glu Gly Ala Cys Asp Leu Thr Pro Asn
        530                 535                 540
Pro Pro Gly Cys Thr Glu Glu Gln Lys Pro Glu Ala Glu Arg Leu Cys
545                 550                 555                 560
Asn Ser Leu Phe Ala Gly Gln Ser Asp Leu Asp Gln Lys Cys Asn Val
                565                 570                 575
Cys His Lys Pro Asp Arg Val Glu Arg Cys Met Tyr Glu Tyr Cys Leu
            580                 585                 590
Arg Gly Gln Gln Gly Phe Cys Asp His Ala Trp Glu Phe Lys Lys Glu
        595                 600                 605
Cys Tyr Ile Lys His Gly Asp Thr Leu Glu Val Pro Asp Glu Cys Lys
    610                 615                 620
Gly Ser Gly Ser Gly Ser His His His His His His
625                 630                 635

<210> SEQ ID NO 2
<211> LENGTH: 21
<212> TYPE: PRT
<213> ORGANISM: Artificial sequence
<220> FEATURE:
<223> OTHER INFORMATION: tag peptide for biotinylation

<400> SEQUENCE: 2

Leu Glu Arg Ala Pro Gly Gly Leu Asn Asp Ile Phe Glu Ala Gln Lys
1               5                   10                  15

Ile Glu Trp His Glu
            20

<210> SEQ ID NO 3
<211> LENGTH: 15
<212> TYPE: PRT
<213> ORGANISM: Artificial sequence
<220> FEATURE:
<223> OTHER INFORMATION: tag peptide for biotinylation

<400> SEQUENCE: 3

Gly Leu Asn Asp Ile Phe Glu Ala Gln Lys Ile Glu Trp His Glu
1               5                   10                  15

<210> SEQ ID NO 4
<211> LENGTH: 21
<212> TYPE: PRT
<213> ORGANISM: Cypridina Luciferase

<400> SEQUENCE: 4

Phe Gln Phe Gln Glu Pro Gly Thr Tyr Val Leu Gly Gln Gly Thr Lys
1               5                   10                  15

Gly Gly Asp Trp Lys
            20

<210> SEQ ID NO 5
<211> LENGTH: 8
<212> TYPE: PRT
<213> ORGANISM: Cypridina Luciferase
```

```
<400> SEQUENCE: 5

Gly Ala Val Leu Thr Lys Thr Arg
1               5
```

METHOD FOR PRODUCING COMPLEX OF BIOTIN-LABELED *CYPRIDINA* (*CYPRIDINA NOCTILUCA*) LUCIFERASE WITH STREPTOAVIDIN AND METHOD FOR STABILIZING THE SAME

This application is a Divisional of U.S. application Ser. No. 11/692,134, filed Mar. 27, 2007 now abandoned.

This application claims priority to U.S. application Ser. No. 11/692,134, filed Mar. 27, 2007 which claims the benefit of priority to the U.S. Patent Application No. 60/833,182, filed Jul. 24, 2006, and U.S. Patent Application No. 60/851,422, filed Oct. 13, 2006, the disclosures of all of which are incorporated by reference herein in their entirety.

TECHNICAL FIELD

The present invention relates to biotin-labeled *Cypridina* luciferase, a complex of the biotin-labeled luciferase with avidin or streptoavidin, a method for stabilizing them, and their application to enzyme immunoassays, immunological stainings in tissues, DNA probe methods and receptor assays.

BACKGROUND ART

In recent years, chemiluminescence has been noticed as a detection system with high sensitivity in enzyme immunoassays. Meanwhile, a luminescence quantum yield in biological luminescence such as a luciferin-luciferase reaction is definitely higher than that in a chemiluminescence reaction, and the biological luminescence is thought to be suitable for microanalysis in the enzyme immunoassays. In particular, the quantum yield in the luminescence system in *Cypridina* (*Cypridina noctiluca*) is high and a turnover number of this enzyme is 10 times or more compared with firefly luciferase. Thus, the practical application of *Cypridina* luciferase to the enzyme immunoassays has been studied. Meanwhile, a method for preparing recombinant *Cypridina* luciferase in a large amount and a method for labeling *Cypridina* luciferase with biotin have been already disclosed in Patent document 1. However, in Patent documents 1 to 4 describing *Cypridina* luciferase, no example of the enzyme immunoassays using the biotin-labeled *Cypridina* luciferase was found, and the biotin-labeled *Cypridina* luciferase made according to the method described in Patent document 1 had only about 1.6% activity compared with the activity before modification. From these, it is obvious that the method for labeling *Cypridina* luciferase with biotin disclosed in Patent document 1 is not suitable for making the labeled enzyme applicable to the enzyme immunoassay. Meanwhile, in Patent documents 1 to 3, the method for maleimidizing the *Cypridina* luciferase is disclosed, but the activity of the *Cypridina* luciferase made by a maleimide hinge method was reduced to one tenth or less compared with the activity before the modification (described in Conventional Art in Patent document 4), and no amplification of signals by an avidin-biotin complex (ABC method) was obtained. Meanwhile, the enzyme immunoassay of the *Cypridina* luciferase utilizing a monoclonal antibody which recognizes *Cypridina* luciferase disclosed in Patent document 4 requires its high cost, and its practical application is not accomplished. Therefore, the development of a method for modifying *Cypridina* luciferase, which is suitable for the enzyme immunoassay, inexpensive and effective is desired.

Patent document 1: JP Hei-5-64583-A
Patent document 2: JP Hei-5-113443-A
Patent document 3: JP Hei-7-98316-A
Patent document 4: JP Hei-8-262021-A

DISCLOSURE OF THE INVENTION

It is an object of the present invention to provide technologies for labeling *Cypridina* luciferase by exploiting a *Cypridina* luminescence system and for stabilizing the labeled luciferase.

It is the object of the present invention to provide the following inventions.

[1] A method for producing *Cypridina* luciferase labeled with biotin, characterized in that a biotin reagent containing a polyalkylene glycol structure as a spacer is reacted with *Cypridina* luciferase.

[2] The method according to [1] above wherein polyalkylene glycol is polyethylene glycol.

[3] The method according to [1] above wherein a position corresponding to a lysine residue K180 and/or K203 in the *Cypridina* luciferase in SEQ ID NO:1 has been biotinylated.

[4] A method for producing *Cypridina* luciferase wherein a sugar chain moiety has been biotinylated, comprising a step of introducing an aldehyde group in the sugar chain moiety by treating *Cypridina* luciferase having a sugar chain with a periodate salt and a step of subsequently reacting the aldehyde group in *Cypridina* luciferase having the sugar chain with a biotinylation reagent which selectively reacts with the aldehyde group.

[5] Biotinylated *Cypridina* luciferase which is *Cypridina* luciferase labeled with biotin having either
(i) a structure wherein *Cypridina* luciferase is linked with biotin through a spacer comprising a polyalkylene glycol moiety; or
(ii) a structure wherein *Cypridina* luciferase having a sugar chain is linked with biotin through the sugar chain.

[6] The luciferase according to [5] above wherein polyalkylene glycol is ethylene glycol.

[7] The luciferase according to [5] above wherein a position corresponding to a lysine residue K180 or K203 in the *Cypridina* luciferase in SEQ ID NO:1 has been biotinylated.

[8] The *Cypridina* luciferase labeled with biotin according to [6] above wherein the polyalkylene glycol structure is represented by the following formula:

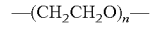

wherein n represents an integer of 2 to 500.

[9] The *Cypridina* luciferase labeled with biotin according to [8] above wherein n is 2 to 100.

[10] A complex of the *Cypridina* luciferase labeled with biotin according to any of [5] to [9] above with a polyvalent avidin substance.

[11] The complex according to [10] above wherein the polyvalent avidin substance has been labeled.

[12] A stabilization composition of the complex according to [10] above comprising the complex and at least one stabilizer selected from the group consisting of surfactants and albumin.

[13] The composition according to [12] above which is in a form of a buffer solution.

[14] A method for stabilizing the complex according to [10] above characterized in that the complex and at least one stabilizer selected from the group consisting of surfactants and albumin are dissolved in a buffer solution.

[15] The method according to [14] above characterized in that the surfactant is combined at about 0.1 to 1%.

[16] A kit for immunoassays including a buffer solution comprising the complex according to [10] above and a stabilizer selected from the group consisting of surfactants and albumin.

[17] The kit according to [16] above which is for measurement by ELISA.

[18] A method for producing tagged *Cypridina* luciferase labeled with biotin, wherein a lysine-containing tag peptide is linked to a C terminus or N terminus of *Cypridina* luciferase and the lysine contained in the tag peptide is biotinylated using biotin protein ligase (EC. 6.3.4.15).

According to the present invention, it is possible to label *Cypridina* luciferase with biotin with keeping a luciferase activity as possible. It is also possible to sufficiently stabilize a complex of the resulting *Cypridina* luciferase labeled with biotin and a polyvalent avidin substance such as avidin, streptoavidin or NeutrAvidin. The complex can be used suitably for immunoassays (in particular, enzyme immunoassays such as direct methods, indirect methods, sandwich ELISA and ELISPOT methods), DNA probe methods, or various assays for receptors, ligands and sugar chains, in particular, assays for quantifying proteins and DNA.

BEST MODES FOR CARRYING OUT THE INVENTION

Figure 1:
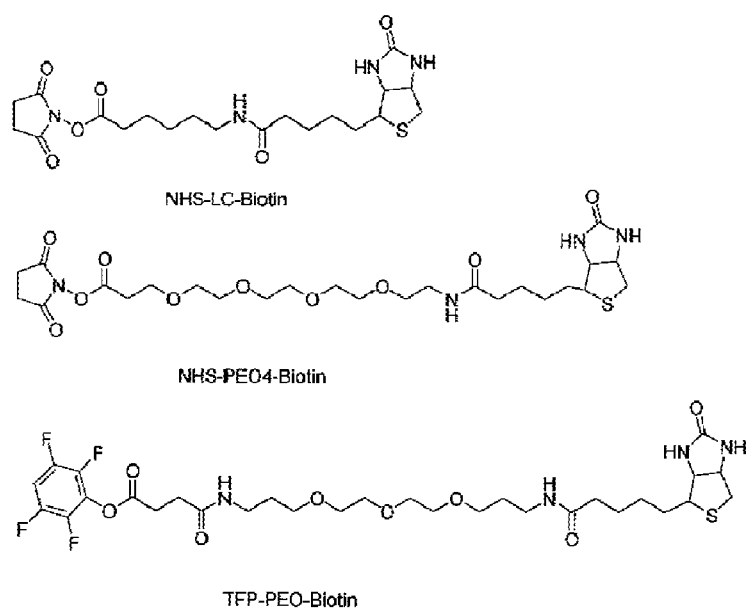
FIG. 1: biotinylation reagents.

*Cypridina* (*Cypridina noctiluca*) luciferase used in the present invention is known publicly. In the present specification and claims, "*Cypridina* luciferase" includes widely wild type *Cypridina* luciferase and optional variants thereof. An amino acid sequence of the wild type *Cypridina* luciferase is described in AAB86460, AAA30332, BAD08210 and the like.

The *Cypridina* luciferase variant may have one or multiple, preferably one or several substituted, added, deleted or inserted amino acid residues, and includes optional variants as long as the variant has a luminescence activity when *Cypridina* luciferin is used as a substrate.

In the present invention, biotin may be bound through any of an amino group (amino group at the N-terminus or derived from Lys), a guanidino group (Arg) or a thiol group (Cys) of *Cypridina* luciferase, and is preferably bound to *Cypridina* luciferase through the amino acid group.

The preferable amino acid group to which biotin is bound is F180 and/or K203 of the amino acid sequence of AAB86460, and in the case of other *Cypridina* luciferase, the amino group at positions corresponding thereto is biotinylated.

The sequence (SEQ ID NO:1) of *Cypridina* luciferase is shown below (K180 and K203 are represented by underlines).

MRFPSIFTAVLFAASSALAALVNTTTEDETAQIPAEAVIGYSDLEGDF
DVAVLPFSNSTNNGLLFINTTIASIAAKEEGVSLEKREAEAQDCPYEP
DPPNTVPTSCEAKEGECIDSSCGTCTRDILSDGLCENKPGKTCCRMCQ
YVIECRVEAAGWFRTFYGKRFQFQEPGTYVLGQGT<u>K</u>GGDWKVSITLEN
LDGTKGAVLT<u>K</u>TRLEVAGDIIDIAQATENPITVNGGADPIIANPYTIG
EVTIAVVEMPGFNITVIEFFKLIVIDILGGRSVRIAPDTANKGMISGL
CGDLKMMEDTDFTSDPEQLAIQPKINQEFDGCPLYGNPDDVAYCKGLL
EPYKDSCRNPINFYYYTISCAFARCMGGDERASHVLLDYRETCAAPET
RGTCVLSGHTFYDTFDKARYQFQGPCKEILMAADCFWNTWDVKVSHRN
VDSYTEVEKVRIRKQSTVVELIVDGKQILVGGEAVSVPYSSQNTSIYW
QDGDILTTAILPEALVVKFNFKQLLVVHIRDPFDGKTCGICGNYNQDF
SDDSFDAEGACDLTPNPPGCTEEQKPEAERLCNSLFAGQSDLDQKCNV
CHKPDRVERCMYEYCLRGQQGFCDHAWEFKKECYIKHGDTLEVPDECK
GSGSGSHHHHHH

The polyvalent avidin substance used in the present invention could link another biotin containing compound such as a biotinylated antibody and a biotinylated antigen with the biotinylated *Cypridina* luciferase, and streptoavidin is preferably exemplified. In addition to it, polyvalent avidin substances such as NeurAvidin and fusion proteins binding multiple avidin molecules, capable of being bound to multiple biotin molecules are widely included.

I. Binding of Biotin to *Cypridina* Luciferase

*Cypridina* luciferase is bound to the biotin residue through the spacer having the polyalkylene glycol structure. Polyethylene glycol includes polyethylene glycol (PEG), polypropylene glycol (PPG), polybutylene glycol (PBG), (PEG)-(PPG)-(PEG) block copolymers, (PPG)-(PEG)-(PPG) block copolymers, (PEG)-(PBG)-(PEG) block copolymers, and (PBG)-(PEG)-(PBG) block copolymers. Preferably, PEG, PPG, the (PEG)-(PPG)-(PEG) block copolymers, and the (PPG)-(PEG)-(PPG) block copolymers are included, and more preferably PEG is included. The preferable PEG structure is represented by the following formula:

—(CH$_2$CH$_2$O)$_n$— wherein n represents an integer of 2 to 500, preferably 2 to 100, more preferably 2 to 50 and still more preferably 4 to 10.

The spacer of the present invention has the polyalkylene glycol structure. It is preferable that the polyalkylene glycol structure is bound to biotin and *Cypridina* luciferase through an ester, amide or thioether bond, preferably the amide bond.

As biotin labeling reagents, for example, the followings can be used.

X1-Y—(CH$_2$)m1-(OCH$_2$CH$_2$)m2-NH-(biotinyl)
X2-Y—(CH$_2$)m1-(OCH$_2$CH$_2$)m2-NH-(biotinyl)

wherein X1 represents an active ester residue (such as sulfo succinic acid imideoxycarbonyl group, succinic acid imideoxycarbonyl group, tetrafluorophenoxycarbonyl, cyanomethyloxycarbonyl p-nitrophenyloxycarbonyl) or a halogen atom (I, Br, Cl) capable of forming amide (NHCO) or aminoalkyl by reaction with an amino group, or a maleimide group; Y represents an optional liking group such as CH$_2$CONH, CH$_2$CH$_2$CONH or a single bond; m1 represents 2, 3 or 4; and m2 represents an integer of 2 to 500, preferably 2 to 100, more preferably 2 to 50 and still more preferably 4 to 10).

As the biotin labeling reagent capable of introducing the polyalkylene glycol group, various biotin labeling reagents such as EZ-Link NHS-PEO4 biotinylation kit and EZ-link TFP-PEO biotinylation kit supplied from Pierce are exemplified.

In a biotin labeling reaction, the biotin labeling reagent as the above could be reacted with *Cypridina* luciferase at 1 to 37° C. and preferably at room temperature. In *Cypridina* luciferase labeled with hydrophilic biotin of the present invention, 1 to 10 biotin residues, preferably 2 to 5 and more preferably 2 to 3 biotin residues per *Cypridina* luciferase are bound to luciferase. If too many biotin residues are bound to luciferase, *Cypridina* luciferase is easily deactivated, and a *Cypridina* luciferase ratio per biotin is reduced.

*Cypridina* luciferase has about 30 lysine residues per molecule. It is possible to introduce biotin by utilizing the reaction of the lysine residue in *Cypridina* luciferase with N-hydroxysuccinimide (NHS) ester. However, a condition to avoid deactivation of luciferase must be established at that time. In particular, the lysine residue is a hydrophilic residue, but a hydrophobic portion is generated on the protein surface after chemical modification. The hydrophobic portion affects a three dimensional structure of the enzyme. Thus, it is effective to introduce biotin through the hydrophilic spacer. The hydrophilic spacer includes alkylene residues having 4 or less, preferably 3 or less, particularly 2 or 3 carbon atoms, represented by —(CH$_2$CH$_2$)$_n$—. The alkylene residue can be linked with an optional group (particularly a polar group) such as O, NH, CONH and NHCO comprising a hetero atom.

II. Binding of Biotin to Tagged *Cypridina* Luciferase

In addition to the method of biotinylating the lysine residue by the above chemical modification, the method of using a tag (peptide) is known. The tag is added to the C terminus or the N terminus of *Cypridina* luciferase, and the lysine residue contained in the tag is specifically biotinylated using biotin ligase. Commercially available such tags include, but are not limited to Avi-tag™ (LERAPGGLNDIFEAQKIEWHE or GLNDIFEAQKIEWHE) supplied from Genecopoeia and BioEase Tag™ (peptide of 72 residues [amino acid residues 524 to 595] of a partial C terminal sequence of α-subunit of oxaloacetate decarboxylase in *Klebsielia pneumoniae*) supplied from Invitrogen.

III. Biotinylation of *Cypridina* Luciferase through Sugar Chain

When *Cypridina* luciferase which is a secretory type glycoprotein is expressed in yeast and animal cells (insects and mammals), *Cypridina* luciferase binding a sugar chain is obtained. When a periodate salt such as NaIO$_4$ is reacted with this sugar chain, a diol group in the sugar chain is oxidized and an aldehyde group is introduced in this sugar chain portion. By reacting with a biotinylation reagent having a group (e.g., hydrazide group, CONHNH$_2$) which selectively reacts with the aldehyde group, it is possible to selectively introduce biotin into the sugar chain without reacting with the side chain amino group of Lys in *Cypridina* luciferase. Biotin can be bound by reacting the aldehyde group with amino group in the biotinylation reagent to convert into imine and reducing this with NaBH$_3$CN.

This method is preferable because biotin is introduced into the sugar chain and thus the biotinylation can be performed with keeping the *Cypridina* luciferase activity. The periodate salt includes sodium periodate, potassium periodate and lithium periodate.

The diol group contained in the sugar chain is oxidized and cleaved by oxidizing 0.5-10 mg of the sugar chain-containing *Cypridina* luciferase with 2-6 mg of NaIO$_4$. By utilizing the resulting aldehyde group, it is possible to selectively biotinylate the sugar chain in *Cypridina* luciferase. The introduction of biotin into the sugar chain can be performed according to, for example, the following scheme 1.

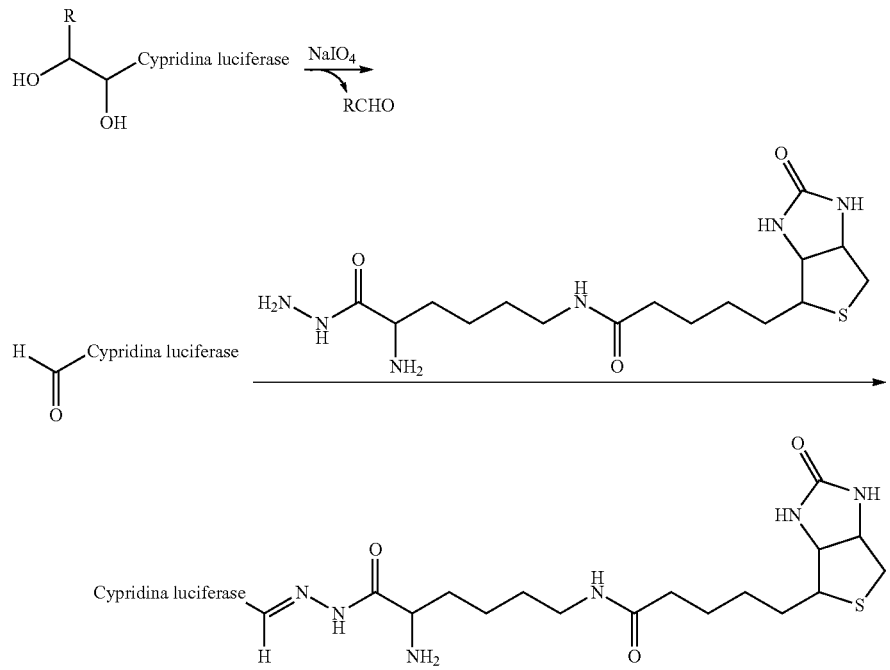

<Scheme 1> wherein, R represents a group derived from the sugar chain and *Cypridina* luciferase has a part of the sugar chain.

Two types of biotinylation reagents are commercially available from Pierce in addition to the above biotinylation reagent.

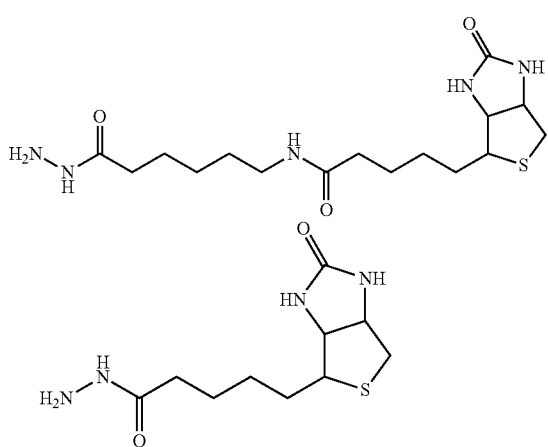

The above biotinylation reagents are only exemplifications, and any reagents may be used as long as the reagent has the group which selectively reacted with biotin and the aldehyde group.

*Cypridina* luciferase labeled with biotin of the present invention forms a complex with avidin, streptoavidin or NeutrAvidin, the complex is further bound to an antibody, an antigen, DNA, a protein (e.g., protein capable of recognizing biomaterials such as receptors, amyloid, synuclein, matrix degrading enzymes, hormones and cytokines), sugar chains (e.g., sialyl Lewis X), substances such as ligands (e.g., hormones, cytokines, lymphokines, prostaglandin, thromboxane, leukotriene, corticosterone, prolactin, endothelin, insulin and the like) capable of recognizing cells or receptors, to which biotin has been bound, and these substances to which biotin has been bound can be used for various assay systems including immunoassays.

*Cypridina* luciferase labeled with hydrophilic biotin of the present invention can form the complex with the polyvalent avidin substance such as streptoavidin, which can be then stored in this state (particularly, buffer solution). The complex can be stored in the buffer solution such as phosphate buffer, tris buffer, acetate buffer and Good buffer (pH 4.0 to 8.0). The complex of *Cypridina* luciferase labeled with hydrophilic biotin with the polyvalent avidin substance can be sufficiently stably stored at 4° C. for about 7 to 28 days by adding a stabilizer. The stabilizer can include surfactants, albumin (BSA, HSA), amino acids (glycine, methionine, arginine), sugars (galactose, lactose, sucrose, glucose and fructose), polyethylene glycol, polyvinyl pyrrolidone, polyol, polyglycerine, gelatin, collagen and dextran.

The surfactants include Tweens such as Tween 20 (Poly(oxyethylene)sorbitan monolaurate), Tween 40(Poly(oxyethylene)sorbitan monopalmitate), Tween60(Poly(oxyethylene) sorbitan monostearate) and Tween 80(Poly(Oxyethylene) sorbitan monooleate), N-bis(3-D-gluconamidopropyl) cholamide [BIGCHAP], N,N-bis(3-D-gluconamidopropyl) deoxycholamide [Deoxy-BIGCHAP], polyoxyethylene(9) lauryl ether, octanoyl-N-methylglucamide [MEGA-8], nonanoyl-N-methylglucamide [MEGA-9], decanoyl-N-methylglucamide [MEGA-10], polyoxyethylene(8)octylphenyl ether [Triton X-114], polyoxyethylene(9)octylphenyl ether [NP-40], polyoxyethylene(10)octylphenyl ether [Triton X-100], polyoxyethylene(20)sorbitan trioleate, polyoxyethylene(23) lauryl ether [Brij35], polyoxyethylene(20)cethyl ether [Brij58], n-dodecyl-β-D-maltopyranoside, n-heptyl-β-D-thioglucopyranoside, n-octyl-β-D-glucopyranoside, and n-octyl-β-D-thioglucopyranoside.

An amount of the complex stabilizer combined in the buffer varies depending on types of the stabilizer, and is typically about 0.01 to 5% and more preferably about 0.1 to 1%.

By making the complex of *Cypridina* luciferase labeled with hydrophilic biotin with streptoavidin, it is possible to sensitize the luminescence of *Cypridina* luciferase. That is, since tour biotin molecules can be bound to one streptoavidin molecule, it is possible to make the large complex by reacting streptoavidin with *Cypridina* luciferase labeled with biotin. Multiple luciferase molecules are included in this complex. Thus, it is possible to sensitize the luminescence. The reaction of streptoavidin with *Cypridina* luciferase labeled with biotin is performed at a molar ratio of about 4:1 to 1:4 in a solution at room temperature for 15 to 30 minutes.

*Cypridina* luciferase labeled with biotin or the complex thereof of the present invention can be used for labeling various antibodies such as secondary antibodies, can directly used in place of horseradish peroxidase (HRP)-labeled secondary antibody and alkali phosphatase (AP)-labeled secondary antibody conventionally used, and can be directly used for various immunoassay kits including the antibody labeled with HRP or AP.

The stabilizer for the complex used in the present invention scarcely affects the enzyme immunoassay, and the solution (particularly the buffer) containing the complex and the stabilizer can be used in the assay system such as enzyme immunoassay.

EXAMPLE

The present invention will be described in detail below based on Examples.
Preparation of Labeled Luciferase by Three Types of Biotin Reagents Example 1

NHS-PEG4-biotin reagent purchased from Pierce was dissolved in purified water to make a solution with a final concentration of 1%. The solution (0.002 of 1% NHS-PEG4-biotin was added to 0.018 mL of a solution of 100 mM sodium phosphate and 150 mM NaCl. Subsequently, the NHS-PEG4-biotin phosphate solution (0.01 mL) was added to 0.1 mg of purified luciferase (relative total luminescence activity 3.6× $10^8$ counts), which was then gently stirred at 4° C. for 8 hours. A reaction solution was applied onto a PD-10 column supplied from GE Health, reaction products were eluted with the solution of 100 mM sodium phosphate and 150 mM NaCl, only active fractions were collected (about 2 mL), and unreacted NHS-PEG4-biotin was eliminated. The eluant (0.01 mL) diluted 1000 times and 0.05 mL of 0.001 mM luciferin were mixed to measure the luciferase activity, and 5.7×$10^7$ counts of the relative total luminescence activity was obtained.

Subsequently, according to the method reported in Patent document 1, NHS-LC-Biotin reagent purchased from Pierce was reacted with 0.1 mg of purified luciferase at 4° C. for 8 hours. The reaction solution was applied onto a PD-10 column supplied from GE Health, reaction products were eluted with the solution of 100 mM sodium phosphate and 150 mM NaCl, only active fractions were collected (about 2 mL), and unreacted NHS-LC-Biotin was eliminated. The eluant (0.01 mL) diluted 1000 times and 0.05 mL of 0.001 mM luciferin were mixed to measure the luciferase activity, and $5.8 \times 10^6$ counts of the relative total luminescence activity was obtained. This activity was about 1.6% of the luciferase activity before the modification.

Furthermore, TFP-PEO-Biotin reagent purchased from Pierce was dissolved in the solution of 100 mM sodium phosphate and 150 mM NaCl to make a concentration of 1 mg/0.85 mL. Subsequently, 0.1 mg of purified luciferase was added to 0.01 mL of the TFP-PEO-Biotin solution and reacted at 4° C. for 8 hours. The reaction solution was applied onto the PD-10 column supplied from GE Health, reaction products were eluted, only active fractions were collected (about 2 mL), and unreacted TFP-PEO-Biotin was eliminated. The eluant (0.01 mL) diluted 1000 times and 0.05 mL of 0.001 mM luciferin were mixed to measure the luciferase activity, and $1.0 \times 10^8$ counts of the relative total luminescence activity was obtained. As a result, in this biotinylation method, about 17 times higher activity was observed compared with the activity in the method reported in Patent document 1. In this labeling method, about 28% luminescence activity of purified luciferase has been retained.

Example 2

Figure 2:
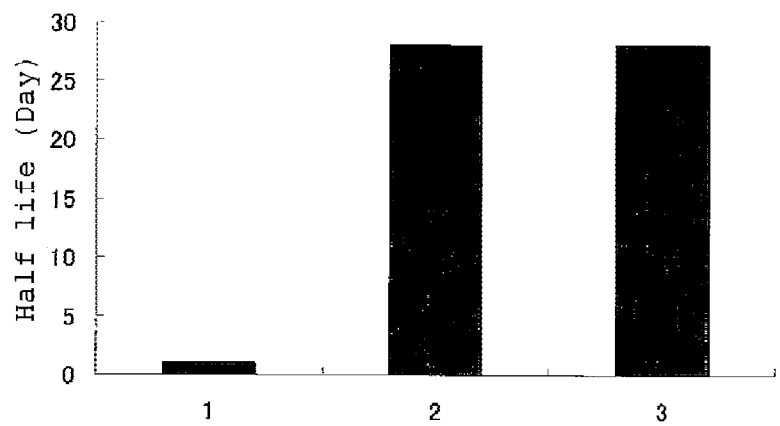
FIG. 2: Half life of biotinylated luciferase in solutions with various compositions. (1) The solution of 100 mM sodium phosphate and 150 mM NaCl, pH 7.2, (2) the solution of 100 mM sodium phosphate and 150 mM NaCl, pH 7.2 containing 0.1% BSA, or (3) the solution of 100 mM sodium phosphate and 150 mM NaCl, pH 7.4 containing 0.1% Tween 20.

Preparation and Storage of Complex of Biotin Labeled *Cypridina* Luciferase with Streptoavidin Molecular weights of luciferase labeled with biotin made in Example 1 and luciferase before the modification were analyzed by mass spectrometer, and about 1,000 mass or more of the molecular weight was observed to be shifted. From this, it was found that about 2 to 3 biotin molecules in average modified one *Cypridina* luciferase molecule. Thus, 0.001 mL of luciferase (0.05 mg/mL) labeled with biotin was mixed with 0.099 mL of the solution of 100 mM sodium phosphate and 150 mM NaCl. Then, 0.1 mL of streptoavidin (1 mg/mL) supplied from Pierce, diluted 1250 times with the solution of 100 mM sodium phosphate and 150 mM NaCl was added to the solution (0.1 mL) of luciferase labeled with biotin, which was then left stand for 15 minutes. Subsequently, 0.04 mL of the reaction solution was added to (1) 0.36 mL of the solution of 100 mM sodium phosphate and 150 mM NaCl, pH 7.2, (2) the solution of 100 mM sodium phosphate and 150 mM NaCl, pH 7.2 containing 0.1% BSA, or (3) the solution of 100 mM sodium phosphate and 150 mM NaCl, pH 7.4 containing 0.1% Tween 20. The mixture was stored at 4° C., and a half life of biotinylated luciferase was examined. As a result, it was found that the half life in the case of the solution (1), the half life was one day whereas the half life in the other solutions was 28 days or more (FIG. 2).

Example 3

Figure 3:
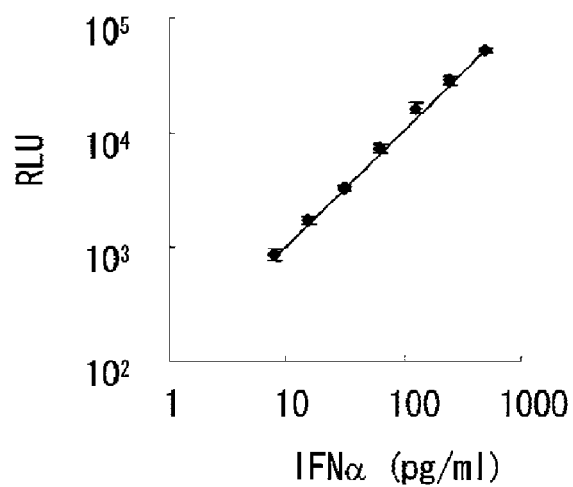
FIG. 3: Quantification property of IFNα ELISA using biotin-labeled *Cypridina* luciferase-streptoavidin complex.

IFNα Assay by ELISA Using Complex of Biotin Labeled *Cypridina* Luciferase with Streptoavidin IFNα was detected using a 96-well microplate to which anti-human IFNα antibody had been immobilized, an IFNα preparation and a biotin-labeled anti-human IFNα antibody contained in an IFNα ELISA kit supplied from GE Health and using the complex of biotin-labeled *Cypridina* luciferase labeled with streptoavidin. A serial dilutions (0.5 mL) of 0, 7.8, 15.6, 31.2, 62.5, 125, 250 and 500 pg/mL of the IFNα preparation were made, and 0.1 mL thereof was added to four rows in the 96-well microplate to which anti-human IFNα antibody had been immobilized. The plate was lightly shaken for one hour, and the solution was removed. Then, 0.15 mL of a solution of 20 mM Tris-HCl pH 7.8, 0.9% NaCl and 0.1% Tween was added to the plate to wash the plate four times. Subsequently, 0.1 mL of the biotin-labeled anti-human IFNα antibody was added to each well, the plate was lightly shaken for one hour, and then the solution was removed. The solution (0.15 mL) of 20 mM Tris-HCl pH 7.8, 0.9% NaCl and 0.1% Tween was added to the plate to wash the plate four times. A solution of biotin-labeled *Cypridina* luciferase with streptavidin made in Example 2 (0.1 mL/well) was added to each well, and the plate was lightly shaken for 30 minutes. The solution was removed, and 0.15 mL of the solution of 20 mM Tris-HCl pH 7.8, 0.9% NaCl and 0.1% Tween was added to the microplate to wash the plate four times. Then, 0.1 mL of 500 nM *Cypridina* luciferin solution was added to the 96-well microplate, and the luminescence was measured. As a result, in serially diluted concentrations (7.8 to 500 pg/mL) of IFNα, a linearity was obtained (FIG. 3). Meanwhile, in the detection system using horseradish peroxidase-streptoavidin contained in the IFNα ELISA kit, the linearity is assured in the range of 25 to 1000 pg/ml. Thus, it was demonstrated that the detection system of the biotin-labeled *Cypridina* luciferase-streptoavidin complex made this time had a higher sensitivity in the measurement.

Example 4

Figure 4:
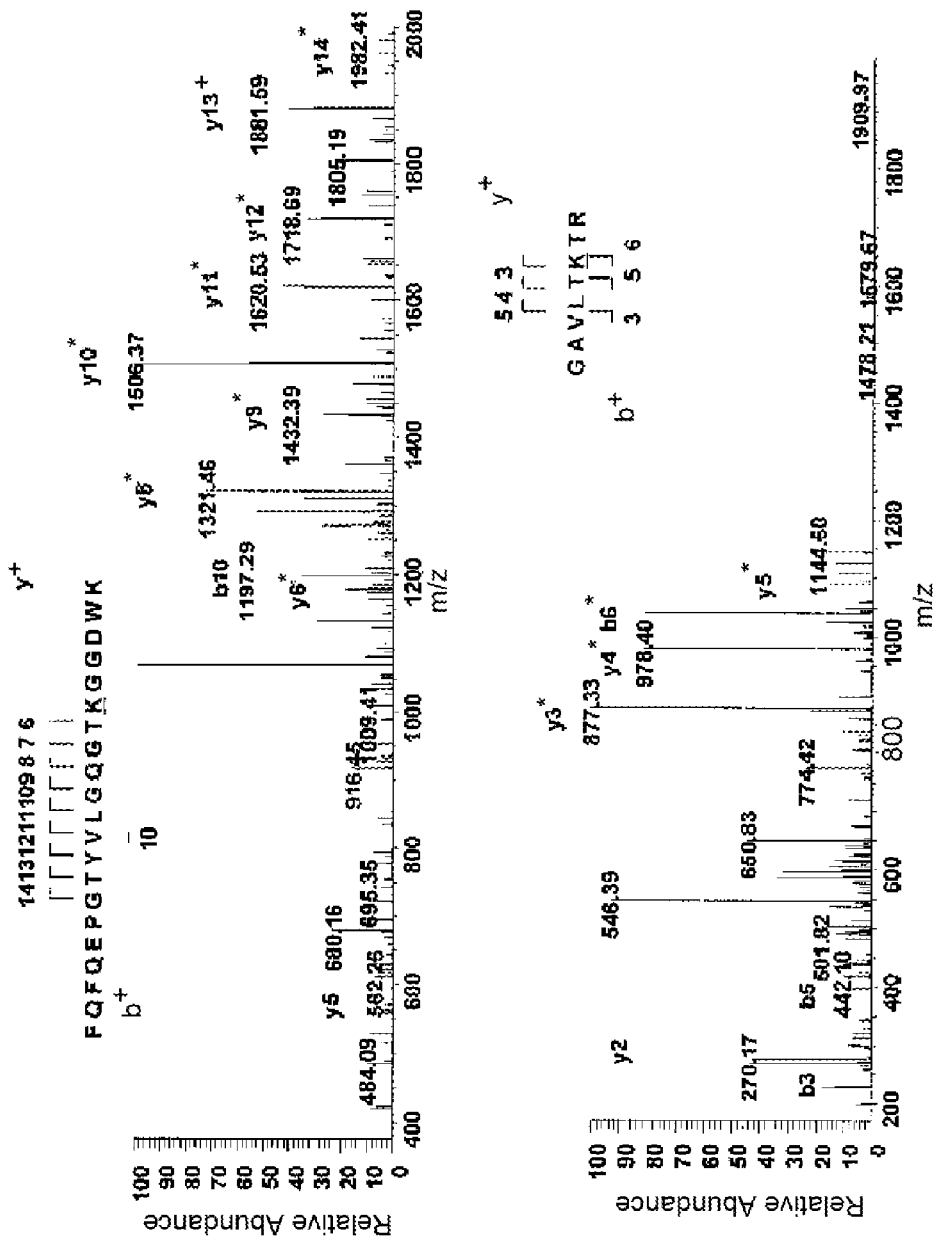
FIG. 4: Results of MS/MS analysis of digested biotinylated *Cypridina* luciferase.

Biotin-labeled *Cypridina* luciferase was electrophoresed on SDS-PAGE, and stained with SYPRO Ruby. A band corresponding to biotin-labeled *Cypridina* luciferase was cut out, cysteine was protected with iodoacetamide, and then luciferase was enzymatically digested with trypsin at 37° C. Resulting samples were analyzed by LC-MS and MS/MS. As a result, the following lysine residues (underlined) were identified to be modified (FIG. 4).

1. FQFQEPGTYVLGQGT<u>K</u>GGDWK

2. GAVLT<u>K</u>TR

Example 5

ELISA Experiment of PGE$_2$ Using Biotin-Labeled *Cypridina* Luciferase

Step 1: Avidinylation of PGE$_2$

PGE$_2$ (molecular weight: 352.46) was dissolved in EtOAc (1 mg/mL), and 0.186 mL of the resulting solution was placed in an Eppendorf tube. EtOAc was vaporized and removed under an argon atmosphere, and 0.05 mL of DMF was added. To that solution, 0.05 mL of a solution of 10 mM N-hydroxysuccinimide (molecular weight: 115.09) in ME was added. Likewise, 0.05 mL of a solution of 10 mM 1-ethyl-3-(3-dimethylaminopropyl) carbodiimide HCl (molecular weight: 191.70) in DMF was added thereto. The mixture was shield from the light by covering with aluminium foil, and left stand at room temperature for 18.5 hours. Subsequently, 0.004 mL of resulting PGE$_2$ active ester was placed in an Eppendorf tube, and DMF was vaporized and removed using a vacuum pump. Then, 0.02 mL of 20 mM potassium phosphate buffer (pH 7.5) was added and mixed thoroughly, subsequently a streptoavidin solution (1 mg/mL, in 0.1 mL 100 mM potassium phosphate buffer, pH 7.2) was added, and the mixture was reacted at room temperature for 30 minutes. An avidin complex with PGE$_2$ was purified using a column for gel filtration.

Figure 5:
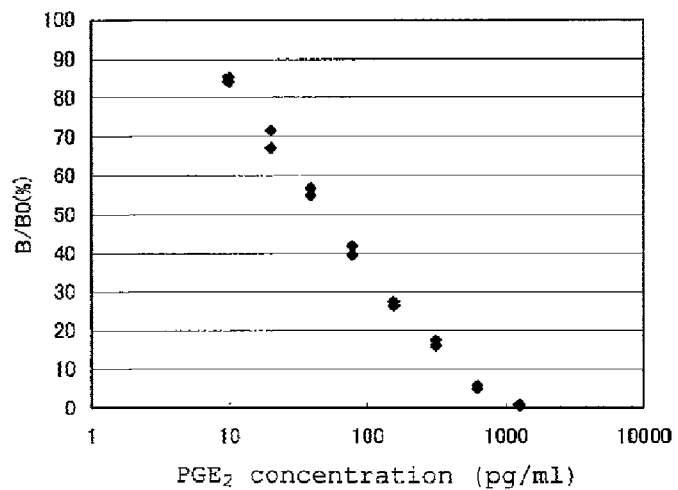
FIG. 5: Competitive reaction ELISA of PGE$_2$.

Step 2: Competitive Reaction ELISA of PGE$_2$ 0.05 mL Of each PGE$_2$ standard solution (10, 20, 40, 78, 156, 313, 625 and 1250 pg/mL), 0.05 mL of anti-PGE$_2$ antibody and 0.05 mL of the avidin complex with PGE$_2$ were dispensed in an immunoplate. The plate was shielded from the light and left stand overnight. On a subsequent day, reaction solutions were discarded, a solution of 20 mM Tris-HCl pH 7.8, 0.9% NaCl and 0.1% Tween 20 was added to each well to wash the wells five times. 0.05 mL of a biotinylated luciferase solution diluted 500 times with 20 mM Tris-HCl buffer pH 7.8 containing 1 mg/mL BSA was added to each well, and the plate was left stand at room temperature for 30 minutes. After 30 minutes, the reaction solutions were discarded, and the wells were washed five times in the same way as the above. Subsequently, 0.1 mL of 0.001 mM luciferin solution (containing 100 mM Tris-HCl buffer, pH 7.4, 300 mM sodium L-ascorbate and 20 mM sodium sulfite) was added to each well and reacted, and a relative luminescence unit (RLU) for 20 seconds was measured using a luminometer JNR (supplied from ATT). As a result, it was found that IC$_{50}$ was 48 pg/mL (FIG. 5).

Example 6

Biotinylation of Sugar Chain in *Cypridina* Luciferase 0.1 mg Of purified luciferase (relative total luminescence activity: 3.6×10$^8$ counts) was dissolved in 0.05 ml of 0.1 M acetate buffer (pH 5.2), which was then mixed with the same amount of 20 mM NaIO$_4$ in 0.1 M acetate buffer (pH 5.2), and the mixture was gently stirred at 4° C. for 0.5 hours. A reaction solution was applied onto the PD-10 column supplied from GE Health, reaction products were eluted with the solution of 100 mM sodium phosphate and 150 mM NaCl, only active fractions were collected (about 2 mL). The solution (2 mL) was concentrated to about 0.02 ml using Biomax 10k supplied from Millipore, and mixed and reacted with 0.02 mL of 10 mM biotin hydrazide (Pierce) in 0.1 M acetate buffer pH 5.2 at room temperature for 2 hours. A reaction solution was applied onto the PD-10 column supplied from GE Health, reaction products were eluted with the solution of 100 mM sodium phosphate and 150 mM NaCl, only active fractions were collected (about 2 mL). 0.01 mL Of the eluant diluted 1,000 times was mixed with 0.05 mL of 0.001 mM luciferin to measure the luciferase activity, and 6.6×10$^7$ counts of the relative total luminescence activity was obtained.

Example 7

ELISA Assay of IFNα Using *Cypridina* Luciferase Whose Sugar Chain has Been Biotinylated IFNα was detected using a 96-well microplate to which anti-human IFNα antibody had been immobilized, an IFNα preparation and a biotin-labeled anti-human IFNα antibody contained in an IFNα ELISA kit supplied from GF Health and using the complex of biotin-labeled *Cypridina* luciferase labeled with streptoavidin. A serial dilutions (0.5 mL) of 0, 7.8, 15.6, 31.2, 62.5, 125, and 250 pg/mL of the IFNα preparation were made, and 0.1 mL thereof was added to four rows in the 96-well microplate to which anti-human IFNα antibody had been immobilized. The plate was lightly shaken for one hour, and then the solution was removed. Then, 0.15 mL of a solution of 20 mM Tris-HCl pH 7.8, 0.9% NaCl and 0.1% Tween 20 was added to the microplate to wash the plate four times. Subsequently, 0.1 mL of the biotin-labeled anti-human IFNα antibody was added to each well, the plate was lightly shaken for one hour, and then the solution was removed. The solution (0.15 mL) of 20 mM Tris-HCl pH 7.8, 0.9% NaCl and 0.1% Tween 20 was added to the microplate to wash the plate four times.

Figure 6:
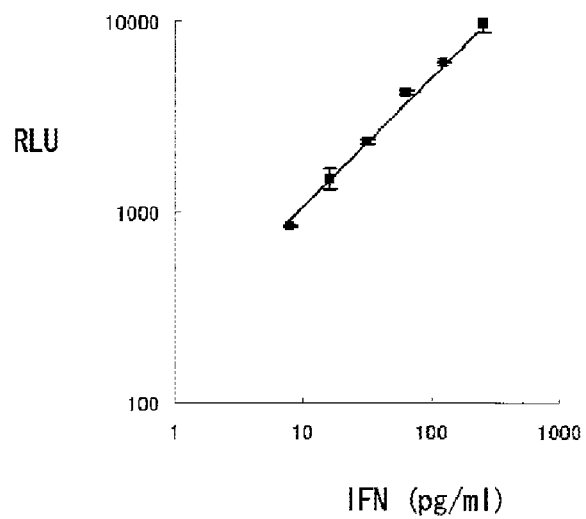
FIG. 6: Quantitative property of ELISA of IFNα using complex of streptoavidin/*Cypridina* luciferase whose sugar chain has been biotinylated.

*Cypridina* luciferase (50 ng/mL) and streptoavidin (30 ng/mL) were mixed at the same amount, and the resulting mixture was diluted 10 times with 0.1 M Tris-HCl pH 7.4/0.1 M NaCl/0.5% BSA. To each well, 0.1 mL of the diluted solution was added, which was then lightly stirred at room temperature for 30 minutes. The solution was discarded, and 0.15 mL of the solution of 20 mM Tris-HCl pH 7.8, 0.9% NaCl/0.1% Tween 20 was added to the microplate to wash the plate four times. 0.1 mL Of 1 μM luciferin was added to the 96-well microplate to measure the luminescence. As a result, the linearity was obtained in the serial dilution 7.8 to 250 pg/mL) of IFNα (FIG. 6).

INDUSTRIAL APPLICABILITY

Inexpensive and effective methods for producing biotin-labeled *Cypridina* luciferase and the complex of biotin-labeled *Cypridina* luciferase with streptoavidin were established. The complex of biotin-labeled *Cypridina* luciferase with streptoavidin, which is excellent in stability can be applied to the field of enzyme immunoassays. The present invention could open the way to exert a feature that *Cypridina* luciferase is highly sensitive.

The invention claimed is:

1. An immunoassay method comprising steps of:
reacting an analyte with a first complex comprising a biotin-labeled *Cypridina* luciferase, a polyvalent avidin substance and an antibody capable of recognizing the analyte, to form a second complex, and
contacting a luciferin with the second complex and measuring a luminescence, wherein:
a biotin of the biotin-labeled *Cypridina* luciferase
is bound at a position corresponding to a lysine residue K180 and/or K203 of SEQ ID NO: 1 via a polyethylene glycol moiety represented by formula —(CH$_2$CH$_2$O)$_n$—
wherein n is an integer of 2 to 50, or
is bound via a sugar chain with a hydrazide linkage;
the biotin-labeled *Cypridina* luciferase is labeled with 2 to 5 biotins; and
the polyvalent avidin substance is selected from the group consisting of avidin, streptavidin and NeutrAvidin.

2. The immunoassay method according to claim 1, wherein the immunoassay method is selected from the group consisting of a direct immunoassay method, an indirect immunoassay method, a sandwich ELISA method and an ELI SPOT method.

3. The immunoassay method according to claim 1, wherein the analyte is a protein or DNA.

* * * * *